United States Patent [19]

Frautschi et al.

[11] Patent Number: 5,017,670
[45] Date of Patent: May 21, 1991

[54] METHODS AND COMPOSITIONS FOR PROVIDING ARTICLES HAVING IMPROVED BIOCOMPATIBILITY CHARACTERISTICS

[75] Inventors: Jack Frautschi, Grand Prairie, Tex.; Kevin Tingey, Salt Lake City, Utah

[73] Assignee: Board of Regents, The University of Texas System, Austin, Tex.

[21] Appl. No.: 100,121

[22] Filed: Sep. 23, 1987

[51] Int. Cl.$^5$ .................. C08G 83/00; A01N 1/00
[52] U.S. Cl. ..................... 527/313; 527/314; 527/315; 523/112; 514/822
[58] Field of Search ............. 527/313, 314, 315; 523/112; 514/822

[56] References Cited

U.S. PATENT DOCUMENTS

| | | | |
|---|---|---|---|
| 3,051,588 | 8/1962 | Lavanchy | 428/246 |
| 3,755,218 | 8/1973 | Yen et al. | 523/112 |
| 3,853,804 | 12/1974 | Yen et al. | 524/233 |
| 4,046,725 | 9/1977 | Pusineri | 523/112 |
| 4,116,898 | 9/1978 | Dudley et al. | 523/112 |
| 4,302,368 | 11/1981 | Dudley et al. | 523/112 |
| 4,415,703 | 11/1983 | Toba et al. | 527/313 |
| 4,501,871 | 2/1985 | Bartl et al. | 527/313 |
| 4,530,974 | 7/1985 | Munro et al. | 525/329.4 |

OTHER PUBLICATIONS

Gaylord, "A Proposed New Mechanism for Catalyzed and Uncatalyzed Graft Polymerization onto Cellulose", *J. Polymer Sci.*: Part C, No. 37, pp. 153–172 (1972).
Huang et al. (1968), *Jrnl. App. Pol. Sci.*, 12:2549.
Munro et al. (1981), T.A.S.A.I.O., 27:499.
Shalaby et al. (1978), *Jrnl. App. Pol. Sci.*, 22:1359.
Hashimoto et al. (1972), *Tetrahedron*, 28:217.
Gore et al., (1970), *Jrnl. Chem. Soc.*, pp. 1343–1345.
Chenoweth et al. (1983), *Kid. Int.*, 24:764.
Eberhart et al. (1982), "Protein Adsorption on Polymers," from *Advances in Chemistry Series* 199, Cooper and Peppas, eds., ACS.
Kabanov et al. (1981), *Polymer Science USSR*, 23:287.
Tingey (1985), *Synthesis Analysis and Albumin Adsorption Properties of Alkylated Poly-4-Vinyl-Pyridine Grafted Polyethylene Terephthalate*, M. S. Thesis.
Frautschi et al. (1983), T.A.S.A.I.O., 29:242.
Munro et al. (1983), A.S.A.I.O., 6:65.
Lubin et al. (1986), PACE, 9:1154.
Tingey et al. (1986), "Alkylated Polyethylene Terephthalate with Enhanced Albumin Affinity," 12th Annual Meeting of the Society of Biomaterials, Minneapolis, Minn., May 29 to Jun. 1, 1986.
Frautschi et al. (1986), "Surface Treatment to Improve Hemodialyzer Reuse," 5th Southern Biomedical Engineering Conf., Shreveport, La., Oct. 1986, Pergamon Press, S. Saha, editor.
*Polyurethanes in Medicine*, (Chapters 5 and 10) Lelah et al., CRC Press, Boca Raton, Fla., 1986.
Frautschi et al. (1987), "Improved Blood Compatability of Alkylated Cuprophan", 13th Ann. meeting of the Society for Biomaterials, Jun. 2–6, 1987, N.Y., N.Y.
Grasel et al. (1987), *Jrnl. Biomed. Mat.*, 21:815.

Primary Examiner—Nathan M. Nutter
Attorney, Agent, or Firm—Arnold, White & Durkee

[57] ABSTRACT

Improved articles having reduced thrombogenicity when in contact with blood products containing albumin and methods of their preparation and use are provided. The articles comprise at the surface of blood contact a water insoluble polymeric substrate material having covalently attached thereon aliphatic extension of 12 to 22 carbon atoms. When exposed to blood, the aliphatic chain extensions provide a hydrophobic binding site for albumin. The articles when implemented with whole blood or blood products selectively enhance albumin affinity binding to the exclusion of other blood components, and subsequently minimize thrombus formation as well as other biocompatibility parameters, such as foreign body immune responses.

14 Claims, 2 Drawing Sheets

METHODS AND COMPOSITIONS FOR PROVIDING ARTICLES HAVING IMPROVED BIOCOMPATIBILITY CHARACTERISTICS

The Government may own certain rights in the present invention pursuant to USPHS grant number R01-HL28680.

BACKGROUND OF THE INVENTION

1. Field of the Invention

The present invention relates to methods and compositions for the production of biocompatible polymers having improved biocompatibility properties. In particular, the invention relates to improved aliphatic hydrocarbon derivatized biocompatible polymers which are established on surfaces of articles adapted for use in contact with blood or blood products.

2. Description of the Related Art

In the past decade, much progress has been made in the development of biocompatible polymers for use in contact with blood or blood products. The general availability of a wide range of polymer types has allowed their implementation in a wide range of medical devices, including, for example, vascular graft tubings, dialysis tubings or membranes, blood bags, tissue prostheses, artificial organs, and the like. Unfortunately, in certain instances, particularly where the article is intended to remain in contact with blood or tissue for extended periods of time, such polymers tend to present various problems associated with physiological and chemical stability and compatability with respect to various contacted tissues and biological fluids.

Both bulk and surface properties determine the functional biocompatibility of the material. Mechanical strength, elasticity, flexibility, creep and fatigue resistance, chemical inertness, impermeability to water vapor, resistance to acid attack, etc. are desired bulk properties of many biomaterials which should be maintained in vivo. The surfaces of exogenous materials in contact with bodily tissues should desirably exhibit resistance to red and white thrombus formation (e.g. blood coagulation, platelet adhesion and aggregation) immunological attack, complement activation, cell adhesion, pannus formation, and the like. These undesirable properties which can result from blood and other tissue interacting with the surface may compromise the intended use of the biomaterial in certain medical devices, and quite possibly result in device failure.

Application of most non-physiologic biomaterials and prostheses to tissue contact initiates a series of physiologic events on the surface of such biomaterials. In particular, a biomaterial such as a synthetic polymer in contact with blood rapidly forms an adsorbed protein layer. Within seconds after application, the biomaterial interface is coated with a thin proteinaceous film, rich in fibrinogen, fibronectin and gamma globulin and other proteins. As blood circulates, further protein components contribute to the thickness of the film. Conformational alterations and complexing of proteins occur, activating defense mechanisms, e.g., coagulation, platelet adhesion and aggregation, white cell adhesion, complement activation etc.

A number of approaches to provide tissue compatibility and specifically blood thromboresistance have been proposed and many promising materials have been developed. However none of the biomaterials developed heretofore have been totally successful and most have provided a poor compromise between device function and long term compatibility.

One such approach has been to modify the surface of existing biomaterials in an effort to prevent endogenous protein adhesion and accumulation so as to avoid coagulation and cell adhesion. Surface modification techniques which have been evaluated for biocompatibility and functionality include low polarity surfaces, glow discharge treated surfaces, negatively charged surfaces, and surfaces coated with biological material, e.g. enzymes, heparin, endothelial cells, and proteins.

The low polarity surfaces such as silicone polymers, and hydrogels, were developed in the view that low surface free energy, specifically low interfacial energy would limit the driving potential for adhesion of proteins and cellular material. Although the silicone biomaterials are substantially chemically inert and improve blood compatibility, platelet aggregation and cell accumulation eventually result with blood contact, especially at low blood flow rates. Glow discharge treated surfaces have temporarily improved the patency of small diameter synthetic vascular grafts. There is no evidence, however, that the effect is of a duration of clinical significance.

Another approach to enhance thromboresistance was to provide materials having negatively charged surfaces. Electrets, hydrogels and negatively charged biological molecules such as heparin, exhibit this property and appear to have improved, but not provide complete thromboresistance. Hydrogels, water saturated polymeric gels exhibiting a net negative surface charge, offer high biological compatibility but by their very nature of high water content lack structural strength and durability.

The biological coated polymers are of considerable interest due to their variability and complexity. Proteinaceous material such as heparin, albumin, and streptokinase have all been covalently bound to polymeric surfaces to enhance thromboresistance. Albumin is of particular interest for a surface coating because of its apparent passivating activity.

Heretofore, albumin has been physically adsorbed, and electrostatically and covalently bound to polymer surfaces. While temporary and partial protection against thrombogenesis is obtained by these methods, the albumin coating is eventually denatured or lost. The loss of albumin functionality when passively adsorbed may be traced to competitive reactions with other proteins having higher affinities for the polymer surface, ablation of the adsorbed albumin, or conformational changes, and fragmentation. Furthermore covalently bound albumin is subject to internal masking by the polymer tertiary structure caused by long term reconstitution of the polymer surface. As the polymer undergoes tertiary reorganization new, unfilled binding sites are presented to which thrombogenic proteins may gain a "foothold".

A further approach which has been taken to improve the thromboresistance of biocompatible polymers is through the alkylation of the polymers with aliphatic hydrocarbon extensions. As shown in U.S. Pat. No. 4,530,974, the addition of aliphatic extensions to the surface of polymers provide thereon a hydrophobic binding site for albumin. Thus, when such articles are implemented with whole blood or blood products, they selectively enhance albumin affinity binding to the exclusion of other blood components, and subsequently minimize thrombus formation.

Unfortunately, the principal methods for hydrocarbon attachment known in the art relate primarily to the addition of hydrocarbon groups to de-protonated amino and imino functions, through the use of a proton abstracting base. This can sometimes present certain disadvantages. For example, the density and distribution of hydrocarbon groups on the resultant derivatized polymer can be limited where amino and/or imino functions are sparsely located within the polymeric structure. Moreover, where the amino and/or imino functions are sterically hindered, or simply unavailable, the polymer can generally not be derivatized in an effective manner.

Other derivatized biocompatible polymers of the prior art have suffered from additional problems, ranging from difficult if not tedious preparation conditions to problems of decreased biocompatibility over extended periods of time. The ideal aliphatic hydrocarbon-derivatized biopolymer exhibits properties of consistently high and "natural" albumin binding with a resultant low activation of coagulation, low complement activation, platelet or white cell adhesion. By "natural" albumin binding is meant binding wherein the aliphatic hydrocarbon-adsorbed albumin molecules tend to retain their natural conformation and hence do not become denatured as readily with time. This allows albumin-adsorbed surfaces to retain their improved surface properties for greatly extended periods of time.

There is currently a great need to provide polymeric surfaces which are biocompatible yet in which some or all of the disadvantages of prior art polymers have been addressed. In particular, there is a need to provide alternative methods for derivatization in the case of biocompatible polymers which contain few accessible amino or imino functions. It is further desirable that these polymer surfaces provide consistent biocompatibility in terms of thromboresistance, resistance to cell adhesion in general and resistance to immunological attack over a range of blood flow rates including status, pH, electrolyte conditions, and hematologic makeups such as anemia, polycythemia, and thrombocytemia.

SUMMARY OF THE INVENTION

It is a general object of the present invention to address at least some of the disadvantages of the prior art by providing aliphatic-derivatized biocompatible polymers having one or more improved properties of biocompatibility.

It is an additional object of the present invention to provide improved methods for preparing such derivatized polymers, which methods provide certain advantages over methods employed in the prior art.

It is a more particular object of the present invention to provide improved aliphatic derivatized polymers of the type which include either aromatic ring moieties or ring structures having adjacent secondary hydroxyl groups within their polymeric structure.

Accordingly, in its general and overall scope, the present disclosure relates to two separate but related invention embodiments, one directed to improved aliphatic derivatized polymers of the type which includes an aromatic ring moiety within its polymeric structure, and the other to improved aliphatic derivatized polymers of the type which includes a ring structure having adjacent secondary hydroxyls within its polymeric structure.

In the first mentioned overall general embodiment, the present disclosure relates to a method for providing an improved biocompatible polymer having an affinity for albumin, the method including generally first selecting a biocompatible polymer whose structure includes an aromatic ring moiety, and derivatizing aromatic moieties of the polymer with aliphatic extensions having between 12 and 22 carbon atoms, wherein the degree of aliphatic derivatization is effective to improve the biocompatibility of the polymer, for example, as may be realized by one or more improved properties of biocompatibility.

As used herein, the term "aliphatic extensions" refers to aliphatic chains of hydrocarbons and include straight or branched unsaturated or more preferably, saturated hydrocarbon chains, namely including alkyl, acyl or olefinic radicals. Thus, it will be appreciated that aliphatic extensions of the present invention are not limited strictly to "hydrocarbons" as this term is strictly employed in the art so long as such extensions retain a minimum level of albumin affinity and confer such an affinity to the selected polymers of the invention. Moreover, as used herein, the term "derivatize" refers to the covalent attachment of such aliphatic extensions to desired polymeric substrates.

With respect to biocompatible polymers whose polymeric structure includes an aromatic moiety, one may maintain by way of illustration polymers such as polyurethanes, polystyrenes, polycarbonates, aromatic polyethers, polyethylene terepthalates or the like. Particularly preferred in certain embodiments herein are biocompatible polymers of the polyurethane type such as may be illustrated by polymers commercially available under the trademarks Pellethane ®, Biomer ® and Avcothane ® or derivatives or modifications thereof.

In certain preferred embodiments, aliphatic derivatization of aromatic moieties is achieved generally by the method of Friedel-Crafts acylation, using alkanoyl halides and in particular, alkanoyl chlorides. By way of illustration, useful alkanoyl (i.e., acyl) groups include those aliphatic alkanoyls having an even number of carbon atoms which are readily available and obtainable from natural sources, such as lauroyl, myristoyl, palmitoyl, stearoyl, arachidoyl or lignoceroyl moieties. However, the embodiment is not limited to such extensions and may be defined generally as aliphatic extensions having the formula $CH_3-(CH_2)_n-(CO)-$, with n ranging from 10 to 20.

As the size of aliphatic extensions narrow from about 12 to 22 carbons to about 16 to 18 carbon atoms the albumin affinity and other biocompatibility properties of the derivatized polymer are found to improve in a step-wise fashion. Accordingly, extensions of increasing or decreasing size to an optimum of 16–18 carbons are particularly preferred for the preparation of biocompatible derivatized polymers in accordance herewith.

Of course, full advantage of the derivatized polymers of the present invention are realized upon contacting the derivatized polymer with a solution such as blood or blood products which includes albumin, in a manner effective to adsorb albumin to its surface, thereby providing a particularly biocompatible surface on the polymer.

In more particular embodiments, the invention is directed to a method for improving the biocompatibility of at least one surface of an article adapted for use in contact with blood or blood products containing albumin, wherein the method includes establishing on such a surface a biocompatible polymeric substrate whose polymeric structure includes aromatic moieties; and derivatizing aromatic moieties of the substrate with aliphatic extensions having between 12 and 22 carbon atoms, and more preferably between 16 and 18 carbon atoms, the degree of derivatization being effective to improve the biocompatibility of said substrate.

The second overall inventive embodiment of the present invention disclosure relates to the aliphatic derivatization of biocompatible polymers whose polymeric structure includes ring structures having adjacent two secondary hydroxyl groups. As used herein, a ring structure having two adjacent secondary hydroxyl groups is defined generally as the sugar subunit of cellulosic polymers. As is known in the art, a secondary hydroxyl group is characterized by the carbon bearing the hydroxyl, which is bound to two atoms other than hydrogen. Accordingly, adjacent secondary hydroxyls refers to their proximity in that they are the distance of the carbon-carbon bond length apart.

Numerous biocompatible polymers having ring structures which include two adjacent secondary hydroxyls are known in the art. By way of illustration one may maintain generally the class of polymers known as cellulosics which include within their structure a hexose ring having a pair of adjacent secondary hydroxyls. Useful polymers include polymers such as cellulose acetate, ethyl cellulose, cellulose nitrate or the like. A polymer type particularly preferred is available under the trademark Cuprophan ®, or derivatives or modified versions thereof.

In certain embodiments herein, a method is therefore disclosed for providing a biocompatible polymer having an affinity for albumin, the method including the steps of selecting a biocompatible polymer whose polymeric structure includes ring structures having adjacent secondary hydroxyl groups; contacting the polymer with a free radical initiator to provide a free radical carbon thereon available for covalent attachment; and derivatizing the polymer at free radical carbons with an organic molecule having within its structure a double bond available for addition to said carbons, the molecule further including, or derivatized to include, at least one aliphatic extension having from 12 to 2,2 carbon atoms, the degree of derivatization of aliphatic extensions being effective to improve the biocompatibility of the polymer.

In certain embodiments, derivatizing the polymer includes free radical addition of aliphatic extensions directly to the provided free radical. In these embodiments, the aliphatic extensions will typically include within their structure a double bond available for free radical addition as well as an extension of from 12 to 22 carbon atoms for adsorption with albumin. Thus, useful aliphatic extensions in this regard would include structures such as terminally unsaturated hydrocarbons.

In other embodiments, aliphatic extensions are derivatized through the use of a graft intermediate. In such embodiments, derivatizing the polymer includes generally adding a graft intermediate having within its structure a double bond available for addition to free radical carbons and a second site available for the addition of aliphatic extensions, and derivatizing second sites of the graft intermediate with aliphatic extensions having from 12 to 22 carbon atoms.

As will be appreciated, the site for addition of aliphatic extensions to graft intermediates may be of various types including, for example, an imino or amino function to which aliphatic extensions are attached in the manner taught by U.S. Pat. No. 4,530,974, an aromatic moiety to which extensions are added as described herein, or the like.

In certain embodiments, the graft intermediate is selected from the group of graft intermediates referenced to generally as substituted vinyls, which includes structures such as vinyl pyridine; styrene; acrylamide; and acrylic acid.

Articles, such as vascular graft tubing dialysis tubing or membrane, blood oxygenator tubing or membrane, intra-aortic balloon, ultrafiltration membrane, blood bag, catheter, suture, soft or hard tissue prosthesis, artificial organ or the like, are improved in accordance herewith by establishing derivatized polymeric substrates of either invention on surfaces adapted for use in contact with body tissues such as blood, or blood products containing albumin.

DETAILED DESCRIPTION OF THE PREFERRED EMBODIMENTS

Figure 1:
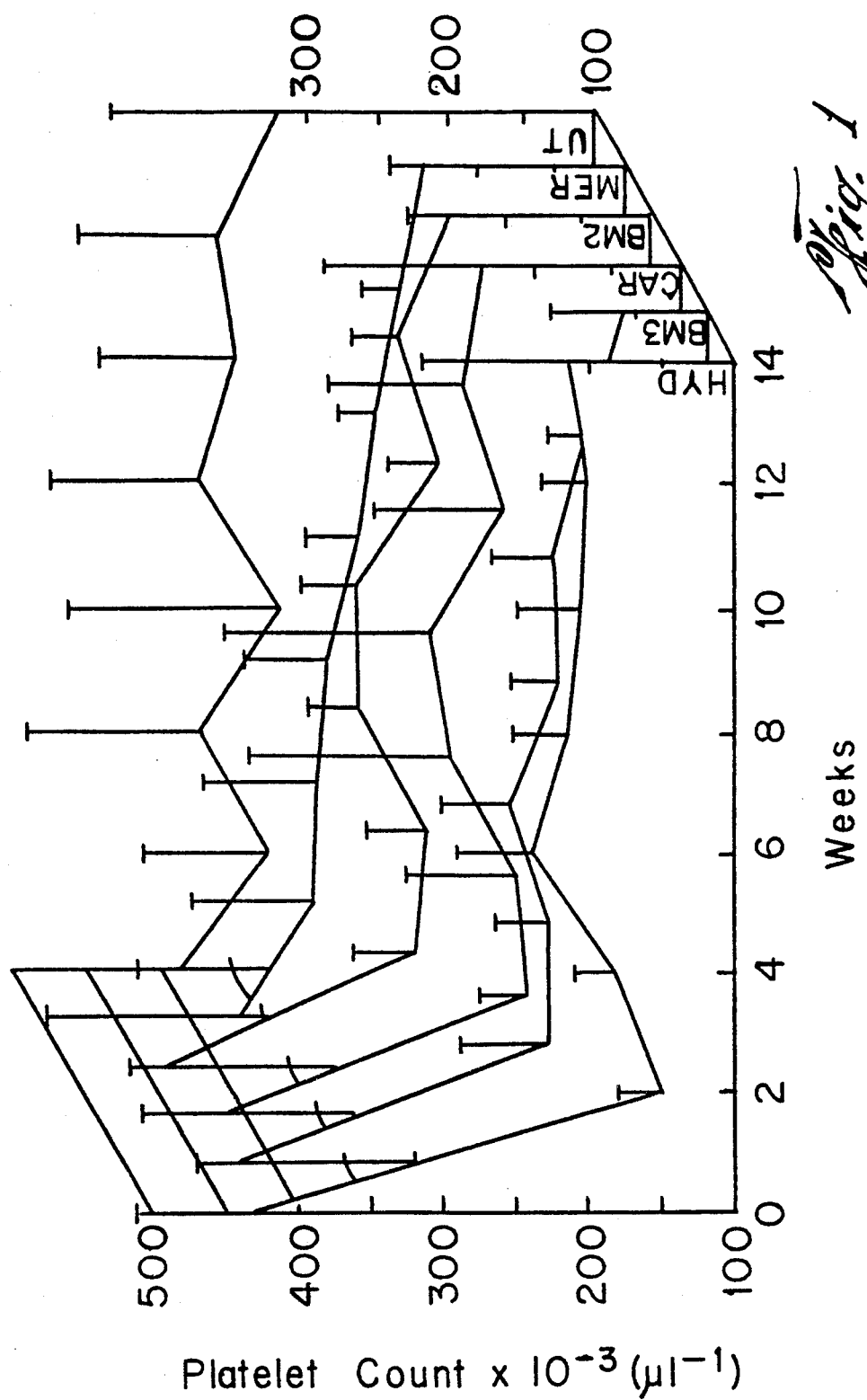
FIG. 1. Circulating platelet count during period of implantation. Bars represent standard deviations. n = 5 for all groups except control for which n = 2. Control group catheters inserted at end of 17-week period for sham operated dogs. See text for details.

The inventions of the present disclosure relate generally to polymeric materials having selective enhancement toward albumin affinity. The practice of the invention provides materials having certain surprisingly good biocompatibility properties including, for example, improved long term characteristics such as reduced deposition of adherent blood product material (e.g., platelets, white cells, fibrinogen, etc.), improved complement activation characteristics, albumin retention, and/or intrinsic coagulatability. These materials are effective when exposed to tissues or blood products containing albumin to selectively bind albumin at the exposed material surface, thereby preventing or reducing the incidence of biocompatibility problems such as thrombus formation or cell adhesion.

It is desirable that the polymer employed, whether of an aromatic moiety type or of a type having ring structures with adjacent secondary hydroxyls, be of a suitable water-insoluble polymer, provided in its solid or semi-solid state. Moreover, it is particularly desirable that the polymer be structurally stable. That is, polymers which have sufficient mechanical strength to be extruded, molded, expressed or formulated into solid construction materials such as films, sheets, conduct tubing, woven meshes or the like.

Suitable polymers of the aromatic type include by way of example, aromatic moiety-containing polymers such as polyurethanes, polystyrenes, polycarbonates, aromatic polyethers, polyethylene terepthalates or the like. Of these polymers, the polyurethanes are preferred. Commercially available polyurethanes include polymers such as Pellethane ®, Biomer ® and Avcothane ® or other derivatives or modifications of polyurethanes such as are known in the art (see, e.g., "Biomedical Polyurethanes" in *Polyurethanes in Medicine*, eds. Lelah and Cooper, CRC Press, Boca Raton, 1986, incorporated herein by reference).

Suitable polymers of the type having ring moieties with adjacent secondary hydroxyls include, more particularly, the class of polymers known as cellulosics, which have hexose rings or related structures having adjacent secondary hydroxyls. Typical useful polymers include those such as cellulose acetate, ethyl cellulose, cellulose nitrate or the like. One particularly preferred polymer is sold under the name Cuprophan ®.

Selection of the polymeric substrate will vary according to the structural and functional needs of the biomaterial device. For example, to prevent thrombus formation on dialysis tubing or membranes, the process of this invention are applied to cellulosic membranes without substantially altering the membranes' original dialysis specifications. Indeed most structural biomaterials in wide application today are amenable to the process of this invention.

Further, these polymers generally have no limitations as to size, shape, or form in which they may be utilized. The polymers may be subject to the derivatization reactions of this invention before or, more preferably, after they are molded or extruded into their final form. In this regard, thin films, sheets, membranes, tubes, hollow fibers, and particulate matter are a few forms which are suitable for use in the present invention.

The aliphatic extensions employed for derivatizing the polymer are preferably of the type having from 12 to 22 carbon atoms, such as aliphatic hydrocarbons or acyls, in that such structures are generally found to adsorb to albumin. More particularly aliphatic extensions of narrowing size ranges of 14–20, 16–20, and so on, are increasingly more preferred, up to an optimal size range of about 16–18 carbons. Although it is believed that unsaturated extensions will prove useful in various embodiments, the more preferred extensions are of the saturated or nearly saturated variety in that these structures more nearly correspond to natural albumin substrates. The most preferred extensions are of the type readily obtainable from natural or commercial sources, such as lauryl, myristyl, palmityl, stearyl, arachidy, or lignoceryl moieties (or lauroyl, myristoyl, etc., and the like). Such structures are also variously referred to as acyl or alkyl halides.

With respect to the treatment of polymers having aromatic structures, such structures are preferably derivatized through the use of a Friedel-Crafts acylation employing an alkanoyl halide (preferably chloride). In general, the acylation is achieved contacting the polymer with, e.g., a treating solution which includes an alkanoyl chloride and a Lewis acid catalyst, such as an aluminum chloride catalyst. The solvent employed is not particularly crucial, so long as it will not hinder the acylation reaction. By way of illustration, one could mention solvents such as trimethyl pentane, nitromethane and carbon disulfide. However, in that "surface" acylation of the polymer is generally preferred over "internal" acylation, it will generally be desirable to choose a solvent in which the polymer will not appreciably swell. It is believed that by swelling the polymer, subsequent aliphatic derivation will not be limited to the surface of the polymer. Hence, it is believed that the resultant polymer surface will not achieve the most optimal biocompatibility properties.

The catalyst employed will generally be dependent upon the solvent used. For example, where a more polar solvent such as nitromethane or nitrobenzene, one will generally desire to use an aluminum chloride catalyst having a compatible polarity, such as aluminum chloride ($AlCl_3$). Where a nonpolar solvent such as trimethylpentane, carbon tetrachloride, or hexane, is employed, one will typically employ a more nonpolar catalyst such as dimethyl aluminum chloride ($Me_2AlCl$). Generally speaking, useful catalysts will include the Lewis acids, which may be exemplified more particularly by $AlCl_3$, $AlBr_3$, $GaCl_3$, $FeCl_3$, etc.

In carrying out the derivatization, it is generally desirable to first form a catalyzing intermediate between the desired alkanoyl chloride and the catalyst, e.g., $Me_2AlCl$. The catalyzing intermediate is formed generally in about 10 minutes at room temperature (with the concentration of catalyst and aliphatic alkanoyl at about 0.05 M). The polymeric composition is then contacted with the catalyzing intermediate, for example by adding the polymer samples to the reaction mixture, or by flowing the reaction mixture through the finished article, for a period of time to allow the desired degree of derivatization. For example, at the aforemention concentrations, it is generally believed that only one alkanoyl side chain is being added to any one aromatic moiety. The degree of derivatization, e.g., the density of derivatization in terms of the ratio of derivatized to underivatized aromatic structures, will generally be determined by the length of time the reaction is allowed to proceed. In most instances, 10 minutes of derivatization under anhydrous conditions will prove adequate to provide improved polymers in accordance herewith.

Care should be taken throughout the procedure to exclude moisture from the reaction. Methods for excluding moisture are well known in the art, and includes such measures as periodically purging the system and performing the reaction under dry nitrogen. Following the reaction, the samples are washed with an appropriate solvent, for example, a 2.5% water-propanol solution and air dried. The type of wash solvent will typically vary depending on the solubility of the by products produced by the catalyst and the acid halide used.

Turning now to a consideration of polymers of the type having ring structures adjacent hydroxyls, such structures are preferably derivatized at a free radical carbon provided at one of said adjacent secondary hydroxyls. This reactive carbon is provided generally by reacting the polymer with a ceric ion catalyst, for example, an ionizable ceric salt such as $CeSO_4$, or ammonium cerium nitrate. The reactive carbon is then derivatized with an organic structure which includes a double-bonded carbon available for reaction with the provided free radical. Most preferablY, such a double bond will be defined by a vinyl group or similar structure, for example, attached to a graft intermediate or directly located at a terminal position of an aliphatic extension.

Accordingly, aliphatic extensions are covalently added to free radical carbons either directly (when they contain, e.g., a terminal vinyl moiety) or through the use of a graft intermediate. As used herein, a graft intermediate is defined as any organic molecule having a vinyl or similar moiety for covalent attachment to free radical carbons, and a second site available for aliphatic derivatization. Thus, such structures include, for example, vinyl pyridine, styrene, acrylamide, or acrylic acid, which, in addition to the vinyl group include an available amino or aliphatic addition, amide or carboxyl, which include aromatic moieties for C12–C22 aliphatic derivatization.

Where a graft intermediate such as vinyl-pyridine is employed for aliphatic attachment, it will be appreciated that the graft intermediate itself will tend to polymerize. Such polymerization serves to add additional sites for aliphatic derivatization and can thus provide even more improved albumin affinity. In the case of 4-vinyl pyridine, graft intermediate polymers of extended length have been found to have a particularly high and stable albumin affinity when derivatized with aliphatic extensions.

The derivatization of polymers of the cellulosic variety such as Cuprophan ® are generally conducted first in an aqueous environment, preferably a slightly acidic environment, such as 1% sulfuric acid, in which medium the cerium ion reaction is carried out. The reaction is performed in a degassed dilute acid solution such as 1% $H_2SO_4$ (v/v) under an $N_2$ blanket. One should be careful to exclude oxygen in that oxygen tends to terminate the reaction. The ceric ion is then adsorbed onto the polymer from a dilute ceric salt solution, such as 2 mM $CeSO_4$ in 1% $H_2SO_4$. Typically, a suitable adsorption is obtained in about 10 minutes at about 45° C. The cerium solution is then removed and the polymer washed with the acid solution without ceric ion.

Where a graft intermediate such as vinyl pyridine is employed, the activated polymer is next contacted with a vinyl pyridine/water solution of the intermediate under conditions of fairly vigorous agitation, generally at a mildly elevated temperature of about 45° C. for one hour or more. It will be appreciated that the degree of intermediate polymerization that occurs, assuming a polymerizable intermediate is chosen, will generally be determined by such factors as the concentration of intermediate and the length of incubation and addition of a free radial terminator. Typically, where vinyl pyridine is employed, a volume to reacting sample surface area is used generally at about 0.0 4 to about 1 ml/cm$^2$ surface area, preferably about 0.06 ml/cm$^2$ surface area.

For the step of aliphatic derivatization, it is generally necessary to perform a solvent exchange to remove the polymer from its aqueous environment and replace it with polar aprotic solvent such as dry dimethylacetamide, dimethyl sulfoxide, tetrahydrofuran or dimethyl formamide. The solvent exchange may be achieved by washing the polymer in an alcohol solution such as methanol at 50° C. for several hours which also acts to remove the more bonded homopolymer which is replaced with the polar aprotic solvent.

Where the polymer contains a polymerized graft intermediate having an imino or amine function such as the heterocyclic nitrogen of pyridine, one may derivatize such structures through the addition of a C12 to C22 alkyl halide, preferably a bromo derivative, to the polymer in the presence of the appropriate polar aprotic solvent. Generally, an alkyl halide concentration of on the order of about 0.6 to 1 M, preferably about 0.8 M, will provide a suitably derivatized intermediate in about 1 to 6 hours, preferably about 6 hours. The haloalkyl sample is then removed, the derivatized polymer washed with solvent and solvent exchanged back to an aqueous environment. The polymer may then be washed with a hydrating solution such as a solution of glycerol, propanol and water (3:15:32), as a final wash and air dried.

It will be appreciated that one advantage to the use of a graft intermediate having a ring nitrogen is that such nitrogen will be in a quarternary form upon aliphatic derivatization. Such a quarternary nitrogen will provide additional advantage in accordance herewith in that these structures are known to be bacteriostatic.

When a graft intermediate such as styrene, acrylamide or acrylic acid is employed, aliphatic derivatization of graft intermediate-derivatized cellulosic polymers may be achieved generally by the manner discussed above in connection with such moieties, with the following modifications styrene derivatized by Friedel-Crafts acylation, acrylamide derivatized by reaction with octodecylisocyanate and acrylic acid derivatized by a DMAP catalyzed acylation.

The examples which follow are illustrative of particularly preferred embodiments for the preparation of derivatized polymers of the inventions disclosed herein. It should be appreciated that many modifications and changes may be made in the reactants, catalysts, conditions and polymers employed herein without departing from the spirit and scope of the invention. Moreover, the examples which follow serve to illustrate certain of the surprising improvements in biocompatibility afforded by these procedures.

EXAMPLE I

C16–C18 Acylation of Pellethane ®

Pellethane ® in the form of a catheter, was extensively washed with ethanol prior to the reaction. The reaction vessel is flushed with dry $N_2$. The catalyst $(CH_3)_2$ AlCl (Aldrich) and palmitoyl chloride, $CH_3(CH_2)_{14}$ (CO)Cl, or stearoyl chloride, $CH_3(CH_2)_{16}$ (CO)Cl, were mixed together in the nonpolar solvent, trimethylpentane (reagent grade, Aldrich) at room temperature, to a concentration of about 0.05 M each. The catalyzing intermediate was formed by incubating these together for about 10 minutes at room temperature. The Pellethane ® sample was then added to the reaction and it was allowed to react for an additional 10 minutes at room temperature. The reaction mixture was purged and the reaction conducted under a dry $N_2$ blanket. Following the reaction, the samples were washed with a 2.5% water-propanol solution and air dried.

EXAMPLE II

Derivatization of Cuprophan ® Using a 4-Vinyl Pyridine Graft Intermediate

The polymer was prepared in a way to remove any nonbonded molecules containing hydroxyls before the reaction. In the case of Cuprophan, glycerol was removed by a water wash. The first step was the ceric ion initiated free radical graft polymerization of 4-vinyl pyridine (Aldrich) onto the surface of the polymer. The reaction was performed in degassed 1% $H_2SO_4$ (v/v) under a blanket of $N_2$ (since $O_2$ terminates the reaction). The ceric ion was adsorbed onto the polymer from a $2\times10^{-3}$ M solution of $CeSO_4$ (Aldrich) in 1% $H_2SO_4$ for 10 minutes at 45° C. The ceric ion solution was withdrawn, membrane washed with degassed 1% $H_2SO_4$, and replaced with a comparable volume of degassed water that was used for the vinyl pyridine grafting. The quantity of vinyl pyridine added was determined by the surface area of the samples (0.059 ml/cm$_2$). The vinyl pyridine was added with vigorous stirring at 45° C. for one hour.

Following the graft polymerization, the samples were washed in methanol at 50° C. for several hours. A solvent exchange was then performed with dry dimethylacetamide (DMA). The alkylation of the grafted polyvinyl pyridine was done in dry DMA at 54° C. under a blanket of $N_2$. Bromohexadecane (Aldrich) at a concentration of 0.75 M was added to react for six hours. The samples were then removed and washed with DMA, which was later solvent-exchanged with water. The samples of Cuprophan should be kept in the hydrated form, so a solution of glycerol, propanol and water (3:15:32) was used as a final wash. The samples were then air dried.

EXAMPLE III

Improved Blood Compatibility of Alkylated Cuprophan ®

A surface treatment as described in Example II was employed to improve the blood compatibility of Cuprophan by increasing the surface affinity for endogenous serum albumin. Poly-4-vinyl pyridine (P4VP) was grafted onto the surface of Cuprophan dialysis membrane followed by $C_{16}$ alkyl derivatization. P4VP determination was varied to provide relatively short (P4VPs) and long (P4VP) intermediate arms. Alkyl substitution of the P4VP graft intermediate at the pyridine ring was carried out to create numerous albumin binding sites. Alkylation of the pyridine ring also creates a quaternary ammonium group, which improves the bactericidal capacity of the material.

Alkyl-derivatized grafted ($C_{16}$-P4VPl), short and long arm P4VP grafted, and unmodified Cuprophan ® membranes were washed, exposed to $^{125}I$ labeled bovine serum albumin solution (BSA, 15 mg/dl) for one minute at room temperature. Samples were washed in degassed phosphate buffered saline (PBS) at 1200 $s^{-1}$ wall shear rate for 30 seconds. Selected samples were further washed with 0.05 N NaOH/ETOH, a protein denaturant. Fresh human serum was prepared and exposed to membrane samples for 40 minutes at 37° C. and analyzed for C3a anaphylatoxin by the method of Hugli (Wagner et al. (1984) *Anal. Biochem.*, 135:75).

Albumin adsorption to derivatized and grafted samples was correlated with previous results, for other $C_{16}$ and $C_{18}$ alkylated polymers (see Munro et al., U.S. Pat. No. 4,530,974; Munro et al. (1983) *Asaio Jrnl,*. 6:65; Frautschi et al. (1983), *Trans. Am. Soc. Artif. Intern. Organs*, 29:242). P4VPI demonstrated enhanced albumin affinity while the shorter armed P4VPs material was no different than control. (Table II). The tenacity of the polymer-albumin bond for derivatized material was demonstrated by the results of treatment with protein denaturant (Table II). These results suggest the conformation of adsorbed albumin is stabilized, even in the presence of strong denaturants, by the (hydrophobic) interaction with the alkyl groups. While P4VPI provides more binding sites for albumin than controls, the bond is less stable than that for $C_{16}$-P4VPl.

A significant reduction in activation of C3 was observed for $C_{16}$-P4VP1 and P4VP1, but not for P4VPs grafted materials, compared with controls (Table II). These results suggest that reduction of complement activation is influenced not so much by removal of surface active hydroxyl groups on Cuprophan ®, but rather from the masking of the surface by endogenous albumin. Quaternization of cetyl derivatized pyridine has previously been demonstrated to improve germicidal capacity against gram-negative and gram-positive bacteria.

These results demonstrate that aliphatic derivatized Cuprophan membranes possess significantly improved resistance to some host defenses of blood.

TABLE I

| Albumin Retention | | |
|---|---|---|
| | Saline Wash | Fraction Retained from NaOH/ETOH Wash |
| Control | 1.0 | 0.26 ± 0.2 |
| P4VPs | 1.10 ± 0.27 | 0.15 ± 0.08 |
| P4VP1 | 3.82 ± 0.5* | 0.26 ± 0.03 |
| $C_{16}$-P4VP1 | 4.20 ± 1.20* | 0.70* ± 0.01 |

*$p < 0.05$ with respect to control

TABLE II

| Complement Activation | | |
|---|---|---|
| | C3a (ug/ml) | C3a Reduction (% of Control) |
| Control | 67.7 ± 16.6 | 100.0 |
| P4VPs | 61.1 | 91.1 |
| P4Vp1 | 50.5 ± 18.0 | 74.1 |
| $C_{16}$-P4VP1 | 25.7 ± 7.3* | 37.2* |

*$p < 0.05$ with respect to control

EXAMPLE IV

Albumin Retention by Derivatized Pellethane ® Catheters

Polyurethane (Pelletheane ®) indwelling catheters (Cook Inc.) were derivatized in the manner of Example I. The derivatized catheters were contacted with a solution of $^{125}I$ labelled bovine serum albumin (15 mg/dl) by static incubation of from 1 minute, so as to allow the albumin to coat the treated surface. Control and $C_{16}$-modified Pellethane ® catheters were then subjected to various washes at a wall shear rate of about 800 $S^{-1}$. The first type of wash was with phosphate buffered saline (PBS). A second wash was a protein denaturant wash of 0.3% SDS, employed to test the stability of albumin adsorbed to the $C_6$ modified catheter. The results are shown below in Table III.

TABLE III

| Albumin Retention of Pellethane ® Catheters[a] | | |
|---|---|---|
| | FRACTION RETAINED | |
| SAMPLE | PBS WASH | 0.3% SDS WASH |
| Control | 1.0 | 0.12 ± 0.01 |
| $C_{16}$-derivatized | 2.10 ± 0.32 | 0.61 ± 0.06 |

[a] n = 4

As will be appreciated, the $C_{16}$ - aromatic moiety-derivatized polymer exhibited high albumin retention relative to control (2.1 fold) and a much higher amount proportionally (5 fold) following the protein denaturant wash.

EXAMPLE V

Prolonged Implantation Study of Derivatized Pellethane

An extended term implant study of the performance of six different polymer surface treatments has been carried out, for application to a pacemaker catheter. The basic implant structure was a fixed tip endocardial pacing lead, 4F ×60 cm (OSCOR Medical) insulated with 4F-80A polyether polyurethane (Pellethane ® 2363-80A, Upjohn). Five of six surface treatments were applied to this insulator. The remaining system was insulated with 6.5F-70A silicone rubber tubing (Vesta Inc.). Surface treatments are listed in Table IV. Pellethane ® samples designated UT were treated as described in Example I. Note that that sample designated MER (Mercor Inc.) is a proprietary bulk additive, incorporated into the polyurethane prior to a special extrusion which provides a very smooth surface.

Each lead was cut into two sections. The section without the corkscrew tip was dipped at both ends in a polyurethane solution made with reagent grade tetrahydrofuran or silicone rubber solution, as appropriate; this segment was subsequently implanted in the inferior vena cava. The cut end of the other segment was similarly treated, but the corkscrew tip and proximal 3 cm was neither dipped nor surface treated, and thus served as a control. The surface of the bulk additive treatment catheter was approximated to this condition by dipping in the polyurethane solution. All devices were washed in 70% methanol and sterilized with ethylene oxide, except for the Hydromer coated devices, which were treated with approximately 3 Mrad gamma irradiation.

TABLE IV

CATHETER TREATMENTS FOR 17-WEEK IMPLANT STUDY

| | Source | Bulk Polymer | Surface Treatment |
|---|---|---|---|
| Control | Upjohn | Pellethane-2363-80A* | None |
| UP | University of Texas Health Science Center | Pellethane-2363-80A | $C_{18}$ alkylation |
| MER | Mercor, Inc. | Pellethane + < 3% proprietary amphipathic additive | None |
| 102 | Biomaterials International | Pellethane 2363-80A | High polyether content polyurethane |
| CAR | Carmeda | Silicone rubbet | Heparin |
| HYD | Hydromer, Inc. | Pellethane 2363-80A | Polyvinylpyrrolidone |
| 103 | Biomaterials International | Pellethane 2363-80A | 60% higher polyether content polyurethane |

Fourteen month old colony bred female beagles (11 kg, LRE Inc.) were acclimatized in pairs for two weeks to outdoor runs. Animals were prepared for aseptic surgery, employing standard techniques. Blunt dissection and cautery were employed to minimize surgical trauma. The devices were introduced into the inferior vena cava (IVC) via the left femoral vein, placing the tip 5-8 cm below the diaphragm. Devices were introduced into the right ventricle via the right external jugular vein, fixing the corkscrew into the apical endocardium. All devices were sutured in place at the entry site, excess implant material was trimmed and the ends were buried subcutaneously. Following radiographic verification of catheter position the wounds were closed in layers.

Fasting venous blood samples were drawn biweekly and analyzed for erythrocyte and differential leukocyte numbers, leukocyte court, platelet numbers, prothrombin time, activated partial thromboplastin time, albumin and fibrinogen concentrations and serum electrolytes. Prior to explantation, animals were anesthetized, systemically heparinized and exsanguinated by axillary arteriotomy. The relevant vasculature was exposed and a complete lengthwise venotomy and ventriculotomy was performed. Following saline rinse, specimens were -photographed in situ, removed and rephotographed, then fixed in buffered formalin (Poly/Lem, Polysciences Inc.).

Heart, lungs and all major pulmonary arteries were examined for thromboemboli: none were found. For microscopic evaluation, sample segments 2.5 cm long were taken 6 cm distal to the sealed IVC tip and 4 cm proximal to the RV helix. For light microscopy, 0.5 cm segments were halved longitudinally, dehydrated in ethanol, and embedded in methacrylate. One micron thick sections were obtained and stained with either hematoxylin and eosin or a modified Carstair's stain for platelets. For SEM, 0.5 cm segments were halved longitudinally, dehydrated through graded acetones and $CO_2$ critical point dried. Samples were then mounted on aluminum slabs and coated with gold pallidium.

Six animals each received two treated catheters: one each at IVC and RV positions. One animal from each group was sacrificed at eight weeks to check that no unusual reactions were taking place. The remaining five animals in each group were sacrificed at 17 weeks. All samples were coded, in order that all personnel involved in catheter implantation, animal handling and surface analysis be unaware of surface treatment. Two animals received sham operations and were followed along with the other groups. Following 17 weeks, these animals received "control" polyurethane tubes from the same lot, which were dip-sealed and sterilized but otherwise untreated; these tubes were introduced into the IVC via the contralateral vein and two animals were maintained an additional eight weeks. Circulating platelet count decreased mildly throughout the implant period for the control group and the alkylated catheter group; decreases for all other groups were much larger (FIG. 1). This is the one remarkable trend in blood parameters. Little variation in serum electrolytes and coagulation parameters was observed between treatment groups over the 17-week implantation period.

Figure 2A:
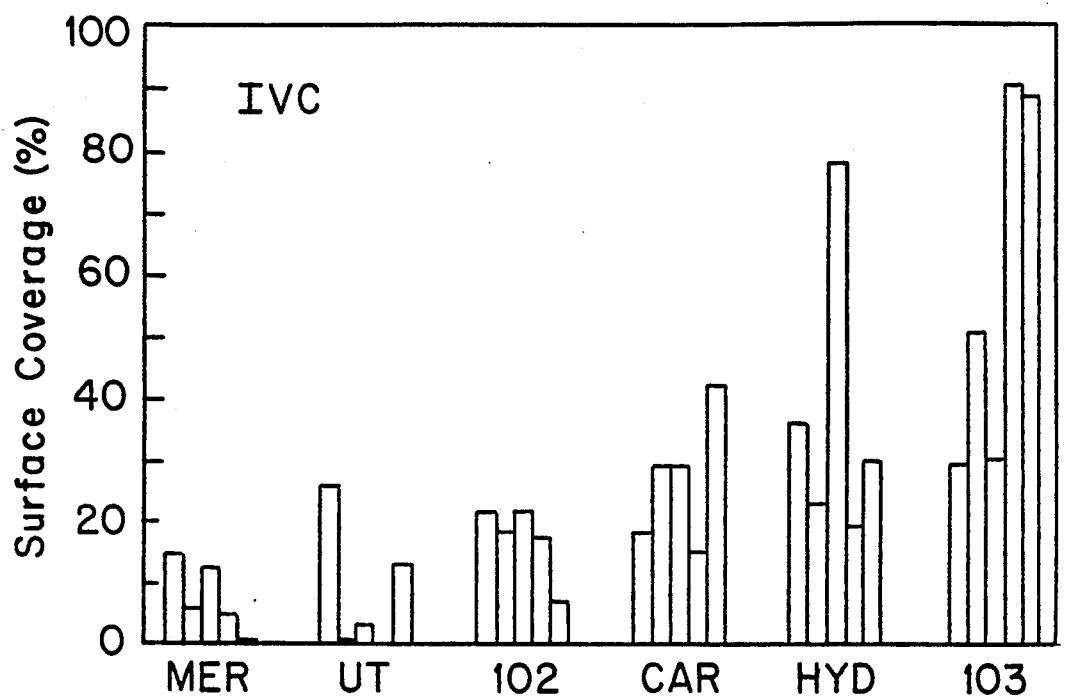
FIG. 2. (a) Surface coverage of catheters implanted in the right ventricle for 17 weeks. (b) Surface coverage of catheters implanted in the inferior vena cava for 17 weeks. Coverage determined by planimetry of enlarged photographs.
Figure 2B:
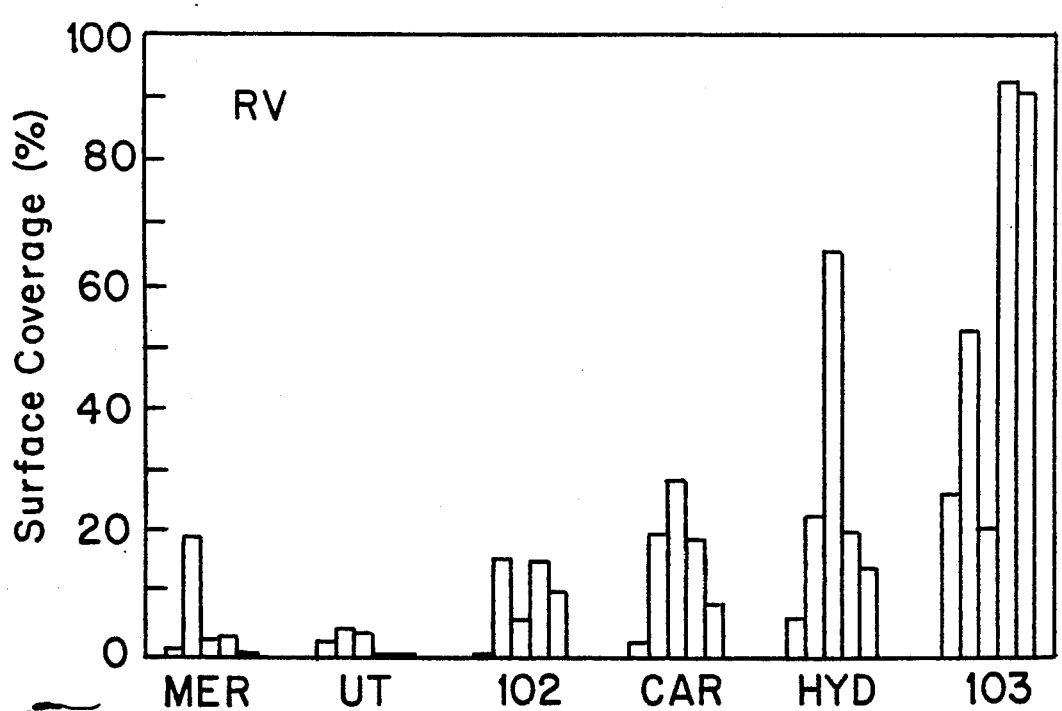

The fraction of the catheter surface encased in tissue, as observed by macroscopic photography, was measured in duplicate by planimetry: results are shown in FIGS. 2a and b. Although group ranking was similar, RV implants generally performed better than IVC implants. Three surface treatments, MER, UT and 102 gave better results by this measure: adherent material was generally limited to the distal half of the catheters in these cases. The three surface treatments with poorer results were observed to have adherent material over the entire length of the catheters. Thrombus on the distal sections of all catheters is expected, since the vein was tied off distal to the insertion site, producing a region of almost stagnant blood up to the vessel branching. Endocardial and valvular lesions were found in the hearts, and endothelial lesions were found in the SVC and IVC of all animals: these were unrelated to the surface treatment. The control dogs had catheters without helical tips and wire cores and showed much less evidence of endothelial trauma in the eight-week implantation. No endocardial cellular proliferations were observed in the left ventricle.

SEM and light microscopic evaluation reiterated the gross analysis and the comparative rankings. Surface roughening was seen to some degree on all implanted, and nonimplanted but treated samples, compared to untreated controls. The group rankings of biological coatings also applied, in general, to the degree of surface roughening. The gross and microscopic examination of the untreated control samples showed them to be at least as low in adherent material coverage as the best treated samples.

Energy dispersive X-ray spectrometry (EDAX) indicated several of the materials with more prevalent biological coatings also developed calcium rich deposits. The bulk additive treatment (MER) yielded the least mineralization of the surface. The alkylated surface treatment (UT) came next in rank. The third ranked treatment in terms of biological coating, 102, developed a pronounced subsurface mineralization, which pushed up the surface.

It was concluded that surface roughness rather than surface treatment was the primary factor influencing growth of a biological layer on these catheters. The improved surface finish and the amphipathic bulk additive probably both contributed to the improved performance of the Mercor catheters. Mild solvent swelling may have improved the surface finish of the alkylated catheters, but solvent evaporation was not controlled to that end. The more probable explanation for the improved performance of the catheters with surface $C_{18}$ alkylation treatment is related to the creation of an endogenous albumin buffer layer. These results are consistent with the findings of shorter term experiments, all suggesting that the endogenous albumin layer adsorbed on $C_{18}$ alkylated surfaces inhibits surface active processes which would otherwise adversely affect the blood contacting material and its host.

A method has thus been developed to enhance the albumin affinity of medical polymers, based on alkylation of the surface with straight chain 16 or 18 carbon alkyl groups. This method has been demonstrated to induce the rapid binding of albumin from single and binary protein solutions, from plasma and, apparently, from whole blood. The bound albumin resists fluid shear- or chemically-induced desorption. Fibrinogen adsorption is inhibited in vitro and in vivo. Complement protein C3 activation from plasma is inhibited. Fibrin formation and platelet aggregation is inhibited in short term in vivo experiments. Long term catheter implant studies suggest that the $C_{18}$ alkylation is more effective than most, if not all currently available treatments for the retention of a clean, biocompatible, blood contacting surface. It is proposed that a renewable albumin layer, so formed, blocks the adsorption or conformational alteration of plasma proteins which otherwise might initiate or participate in various host defences.

EXAMPLE VI

Complement System Passivation With Aliphatic Derivatized Biomer ®

The total hemolytical activity of the serum complement before and after its incubation with polymer is determined by kinetic titration using the photocolorimetric method (Shkurko (1973), *Laboratornoye delo*, 6:327-329, incorporated herein by reference). The registered parameter is the time for 50% lysis ($T_{178}$) of 5 mL of sensitized sheep erythrocytes ($5 \times 10^8$/mL) 100 uL of studied serum. The thermostated sets with stirrers are used to provide the constant temperature (37° C.) and kinetic regime of the reaction. Incubation of the polymer samples with serum, preliminary diluted by veronal-medinal buffer (containing 0.15 mM $CaCl_2$ is conducted in special air tight glass cells. The optimal conditions of the experiment, i.e. incubation time, 90 min, specific surface area, 20 $cm^2$/mL, and the interval of complement activity, providing the constant kinetic regime of the lysis reaction of sheep erythrocytes, is determined in preliminary studies. The initial concentration of the diluted serum should provide complement activity with the value of $T_{178}$ being before incubation 350-450 s, and after incubation not exceeding 800-850 s. Under these conditions the reaction of sheep erythrocytes lysis proceeds by a second-order reaction; i.e., linear correlation between the time for 50% lysis ($T_{178}$) and the value of $1/C_0$ (or $1/A_0$) exists, where $C_0$ is the initial concentration of serum ($A_0$ is the initial complement activity).

The results of this hemolytic assay of complement activation are shown below in Table V. As will be appreciated, the data demonstrates a much reduced complement activation for the derivatized sample as compared to either a Biomer ® or Cuprophan ® control.

TABLE V

| | Complement Activation | |
|---|---|---|
| Material | $k_{ind} \cdot 10^5$ $sec^{-1}cm^{-2}$ | $\bar{k}_{ind}$ |
| BIOMER ® CONTROL | 6.6 | 0.76 |
| DERIVATIZED BIOMER ® | 2.9 | 0.33 |
| 2.0 TIMES ALBUMIN ENHANCEMENT CUPROPHAN ® | 8.7 | 1.00 |

Cuprophan ® was taken as a control.
Experimental conditions: $t_{incub.} = 60$ min; $t^* = 37°$ C.

EXAMPLE VII

Surface Treatment To Improve Hemodialyzer Reuse

Hemodialysis treatment of chronic renal failure is perhaps the most successful application of artificial organs research. However, complications related to this procedure are still observed, such as activation of the immune system via the alternate complement pathway, by cellulosic polymer membranes. Practical problems requiring additional work are also observed, including sterility maintenance for dialyzer reuse applications and improve thromboresistanoe of the dialyzer circuit.

We have investigated a membrane surface treatment which provides significant improvements in dialyzer performance for each of these problem areas. The method is based on the increase in albumin binding to the membrane, caused by grafting 16 carbon alkyl chains to the polymer backbone. Serum albumin regards these chains as equivalent to circulating free fatty acids (palmitic acid), for which it has high affinity. An albumin layer is rapidly and densely adsorbed from blood, inhibiting fibrinogen adsorption and also inhibiting surface contact-activated processes which would otherwise initiate coagulation, platelet adhesion and aggregation, complement activation, etc. We describe in this example results obtained for the alkylation of Cuprophan ® dialysis membrane treated in this manner.

Poly-4-vinyl pyridine (P4VP) was grafted onto Cuprophan ® employing a ceric ion reaction at hydroxyl sites. P4VP was chosen since it is an easily accessible monomer with known properties giving adequate yields in surface graft polymerization. The graft intermediate was alkylated with bromohexadecane, yielding abundant C$_{16}$ side chains. In addition to alkyl yield, the reaction is significant since it can be carried out in an aqueous environment.

The albumin adsorption was assessed in a series of $^{125}$I-labeled protein incubation studies. Iodo-gen ® (Pierce)-mediated oxidation of iodine with subsequent incorporation of generated iodine radicals into albumin tyrosine residues was used. Labeled bovine serum albumin solution (BSA, 15 mg/dl) Was incubated statically for one minute at room temperature with alkylated and grafted, grafted and untreated (control) membranes. Following exposure, membranes were washed in degassed phosphate buffered saline at high flow (1,200 s$^{-1}$ wall shear rate) for one minute.

For complement activation studies, blood was collected from human volunteers into heparin-containing sterile vacutainers. Following centrifugation, serum was incubated with membrane samples for 40 minutes at 37° C. Membrane surface area to serum volume ratio approximated that seen in clinical hemodialysis. After membrane exposure, samples were analyzed by the radioimmunoassay-based complement/activation technique (Hugli and Chenoweth (1980) in *Immunoassays: Clinical Laboratory Techniques*, Alan R. Liss, Inc., N.Y., pp 443–460).

BSA uptake on C$_{16}$ P4VP was 4.4 times control values ($p < 0.005$). BSA uptake on grafted but unalkylated samples was 3.8 times control ($p < 0.05$). Albumin was not desorbed from alkylated grafted samples by sodium dodecyl sulfate washing, but was desorbed from the grafted unalkylated samples by this treatment. BSA affinity for grafted samples was reduced by decreasing P4VP chain length.

C3a for C$_{16}$P4VP was 29% of that for controls ($p<5$). C3a was not significantly different than that observed for the copolymerized but unalkylated samples. Other results with C$_6$ alkylated Cuprophan ® suggest no activation of complement proteins C4 and C5, nor is any such reaction expected.

These results demonstrated that graft copolymerization of Cuprophan ® dialysis membrane followed by C$_{16}$ alkylation promotes rapid adsorption of an albumin layer. The albumin layer significantly decreases activation of complement by the alternate pathway, involving C3 protein. The results also demonstrated that the P4VP graft polymerization followed by C$_{16}$ alkylation promotes the rapid adsorption of an endogenous layer of serum albumin. The albumin layer is shown to significantly reduce activation of complement proteins. The albumin layer is tenaciously held, and resists fluid shear. The results therefore suggest that treatment may inhibit contact activated host defenses during dialysis. In addition, the alkylated pyridine, a quaternary ammonium, functions as a germicidal agent. It is also amenable to ionic binding of other antibiotics to maintain sterility during a period of storage between dialysis sessions.

What is claimed is:

1. A method for providing a biocompatible polymer having an affinity for albumin, the method comprising the steps of:
   (a) selecting a biocompatible polymer whose polymeric structure includes non-aromatic ring structures having adjacent secondary hydroxy groups;
   (b) contacting the polymer with a free radical initiator to provide free radical carbons thereon available for covalent attachment of an organic molecule;
   (c) derivatizing the polymer in an aqueous solution at free radical carbons with an organic molecule to form a grafted polymer intermediate, said organic molecule having within its structure a first site and a second site, said first site being a double bond available for addition to said polymer free radical carbons; and
   (d) derivatizing said organic molecule second site to include at least one aliphatic extension having from 12 to 22 carbon atoms covalently attached to said organic molecule, the degree of derivatization of the organic molecule with aliphatic extensions being effective to improve the biocompatibility of the polymer.

2. The method of claim 1 wherein the biocompatible polymer comprises a cellulosic.

3. The method of claim 1 wherein the biocompatible polymer comprises a cellulose acetate, ethyl cellulose or cellulose nitrate polymer.

4. The method of claim 1 wherein the free radical initiator comprises ceric ions.

5. The method of claim 1 wherein derivatizing the polymer comprises free radical addition of aliphatic extensions to free radical carbons thereon, said extensions having from 12 to 22 carbon atoms and having within their structure a double bond available for free radical addition to said free radical carbons.

6. The method of claim 1 wherein the aliphatic extensions comprise aliphatic extensions of CH$_3$—(CH$_2$)$_n$—, wit n ranging from 11 to 21.

7. The method of claim 1 wherein the aliphatic extensions comprise extensions of lauryl, myristyl, palmityl, stearyl, arachidyl or lignoceryl moieties.

8. The method of claim 5 wherein the graft intermediate includes an abstractable hydrogen site available for covalent attachment.

9. The method of claim 5 wherein the graft intermediate includes an aromatic moiety.

10. The method of claim 5 wherein the graft intermediate includes an imino or amino functional group available for covalent attachment.

11. The method of claim 10 wherein the graft intermediate includes a heterocyclic nitrogen available for covalent attachment.

12. The method of claim 1 wherein the derivatized polymer includes a quarternary ammonium.

13. The method of claim 1 wherein the aliphatic extensions comprise saturated aliphatic extensions.

14. The method of claim 1 wherein the aliphatic extensions comprise aliphatic extensions having from 16 to 18 carbon atoms.

* * * * *

UNITED STATES PATENT AND TRADEMARK OFFICE
CERTIFICATE OF CORRECTION

PATENT NO. : 5,017,670

DATED : May 21, 1991

INVENTOR(S) : Jack Frautschi et al

It is certified that error appears in the above-identified patent and that said Letters Patent is hereby corrected as shown below:

Claim 1, line 19, column 18    delete "alphatic and replace with --aliphatic--.

Claim 6, line 40, column 18    delete "wit" and replace with --with--.

Signed and Sealed this

Twentieth Day of October, 1992

Attest:

DOUGLAS B. COMER

Attesting Officer    Acting Commissioner of Patents and Trademarks